(12) United States Patent
Kim

(10) Patent No.: US 8,481,326 B2
(45) Date of Patent: Jul. 9, 2013

(54) APPARATUS FOR MEASURING CHOLESTEROL AND METHOD THEREOF

(75) Inventor: In Wook Kim, Seongnam-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 72 days.

(21) Appl. No.: 13/179,013

(22) Filed: Jul. 8, 2011

(65) Prior Publication Data

US 2012/0015441 A1    Jan. 19, 2012

(30) Foreign Application Priority Data

Jul. 13, 2010    (KR) ......................... 10-2010-0067308

(51) Int. Cl.
*G01N 33/92* (2006.01)
*G01N 33/53* (2006.01)
*G01N 33/543* (2006.01)
*G01N 1/18* (2006.01)

(52) U.S. Cl.
USPC ............. 436/71; 436/63; 436/175; 436/177; 436/180; 436/501; 436/518; 436/531; 436/534; 436/45; 422/68.1; 422/69; 422/72; 422/502; 422/503; 422/504; 422/506; 422/537; 422/533; 435/11; 435/287.1; 435/287.2; 435/287.3; 435/288.3; 435/288.4; 435/288.5

(58) Field of Classification Search
USPC .................. 436/501, 518, 524, 531, 534, 63, 436/71, 164, 174, 175, 177, 180, 824, 45; 422/68.1, 69, 72, 82.05, 501, 502, 503, 504, 422/506, 507, 527, 533; 435/11, 287.1, 287.2, 435/287.3, 288.3, 288.4, 288.5
See application file for complete search history.

(56) References Cited

U.S. PATENT DOCUMENTS

| | | | | |
|---|---|---|---|---|
| 5,215,886 | A * | 6/1993 | Patel et al. | 435/11 |
| 2002/0192722 | A1* | 12/2002 | Stolowitz et al. | 435/7.9 |
| 2008/0056949 | A1* | 3/2008 | Lee et al. | 422/72 |
| 2008/0166745 | A1* | 7/2008 | Khan et al. | 435/11 |
| 2009/0286327 | A1* | 11/2009 | Cho et al. | 436/174 |
| 2010/0044918 | A1* | 2/2010 | Lee et al. | 264/297.8 |
| 2010/0049022 | A1 | 2/2010 | Parris et al. | |

FOREIGN PATENT DOCUMENTS

| | | |
|---|---|---|
| JP | 2004251673 A | 9/2004 |
| KR | 20020015246 A | 2/2002 |

OTHER PUBLICATIONS

International Search Report (PCT/ISA/210) issued on Feb. 21, 2012 in the International Patent Application No. PCT/KR/2011/004972.

* cited by examiner

*Primary Examiner* — Maureen Wallenhorst
(74) *Attorney, Agent, or Firm* — Sughrue Mion, PLLC

(57) ABSTRACT

A microfluidic device and method for measuring a level of cholesterol therewith are provided. The cholesterol measurement apparatus includes a microfluidic device including a plurality of chambers and at least one channel through which the plurality of chambers are interconnected. The plurality of chambers include a reaction chamber which contains a capture binder, a buffer chamber which contains an elution buffer and is connected to the reaction chamber, and at least one detection chamber which contains a cholesterol measurement reagent and is connected to the reaction chamber.

28 Claims, 3 Drawing Sheets

APPARATUS FOR MEASURING CHOLESTEROL AND METHOD THEREOF

CROSS-REFERENCE TO RELATED APPLICATION

This application claims priority from Korean Patent Application No. 10-2010-067308, filed on Jul. 13, 2010 with the Korean Intellectual Property Office, the entire disclosure of which is incorporated herein by reference.

BACKGROUND

1. Field

Apparatuses and methods consistent with exemplary embodiments relate measurement of cholesterol, and more particularly to an apparatus for measuring a concentration of cholesterol in blood using a binder specifically combined with a lipoprotein, and a method for measurement thereof using the apparatus.

2. Description of the Related Art

A microfluidic device is a device for conducting biological or chemical reactions, using a small amount of fluid.

In general, a microfluidic structure of a microfluidic device has at least one independent function, includes a chamber containing a fluid therein, a channel through which the fluid flows and a valve for controlling flow of the fluid. The microfluidic structure may be fabricated by combining these components in different ways. In particular, a device may have a microfluidic structure mounted on a substrate on a small chip for conducting some experiments involving biological or chemical reactions. Known as a "lab-on-a-chip," this device provides for execution of several experimental processes and/or operations on the structure. In order to move a fluid within the microfluidic structure, a driving pressure is generally required. The driving pressure may be a capillary pressure or pressure generated using a pump. A disc-type microfluidic device having a microfluidic structure mounted on a disc-shaped rotational platform has also been proposed. The disc-shaped microfluidic device uses centrifugal force to move a fluid in order to execute a series of tasks.

Lipids in blood, such as cholesterol, are typically combined with plasma protein, which is often called apolipoprotein, to form lipoprotein. Lipoproteins are classified into several major groups according to their density, including: chylomicrons, very low density lipoprotein (VLDL), low density lipoprotein (LDL) and high density lipoprotein (HDL). Related art methods for determining a concentration of HDL cholesterol in blood are problematic in that they provide low measurement accuracy. The problems occur since the concentration of HDL cholesterol is often measured in combination with other non-HDL cholesterol, which requires repetition of the measurement procedure for the non-HDL cholesterol.

SUMMARY

Exemplary embodiments provide apparatuses and methods for simultaneous measurement of HDL cholesterol and non-HDL cholesterol.

According to an aspect of an exemplary embodiment, there is provided an apparatus for measurement of cholesterol including a micro-fluidic device which includes a plurality of chambers and at least one channel through which the plurality of chambers are interconnected, wherein the plurality of chambers include: a reaction chamber which contains a capture binder; a buffer chamber which contains an elution buffer and is connected to the reaction chamber; and at least one detection chamber which contains cholesterol measurement reagent and is connected to the reaction chamber.

Transfer of a fluid between the plurality of chambers may be controlled using at least one valve.

The valve may include a mixture of a phase transition material and a heating fluid.

The phase transition material may include at least one material selected from a group consisting of wax, gel and thermoplastic resin.

The heating fluid may include carrier oil and numerous micro-heating particles dispersed in the carrier oil, wherein the micro-heating particles may be metal oxide microparticles.

The cholesterol measurement apparatus may further include an external energy source to supply energy to the valve.

The external energy source may include a laser source.

The capture binder may include at least one substance selected from a group consisting of antibodies, antigens, receptors, ligands, oligonucleotides, haptens and aptamers.

The capture binder may be specifically combined with an Apo-B protein of a lipoprotein in a fluid sample to capture a non-high density lipoprotein (non-HDL) and separate it from HDL.

The capture binder may be bonded to a solid phase including agarose gel or polymer beads; however, the capture binder is not particularly limited to such forms.

The reaction chamber may include a reaction region in which the capture binder is placed and fixed thereto.

The reaction region may be formed of at least one selected from a group consisting of a porous membrane, a micro-pore and a micro-pillar.

According to an aspect of another exemplary embodiment, there is provided a centrifugal apparatus for measurement of cholesterol, including: a microfluidic device including a rotational body which includes a plurality of chambers and at least one channel through which the plurality of chambers are interconnected, wherein the plurality of chambers further include: a reaction chamber which contains a capture binder; a buffer chamber which contains an elution buffer and is connected to the reaction chamber; and at least one detection chamber which contains a cholesterol measurement reagent and is connected to the reaction chamber.

Transfer of a fluid between the plurality of chambers may be controlled using at least one valve.

The valve includes a mixture of a phase transition material and a heating fluid.

The phase transition material may include at least one material selected from a group consisting of wax, gel and thermoplastic resin.

The heating fluid may include carrier oil and numerous micro-heating particles dispersed in the carrier oil, wherein the micro-heating particles may be metal oxide microparticles.

The cholesterol measurement apparatus may further include an external energy source to supply energy to the valve.

The external energy source may include a laser source.

The capture binder may include at least one substance selected from a group consisting of antibodies, antigens, receptors, ligands, oligonucleotides, haptens and aptamers.

The capture binder may be bonded to a solid phase including agarose gel or polymer beads, however, the capture binder is not particularly limited to such forms.

The reaction chamber may include a reaction region which may be formed of at least one material selected from a group consisting of a porous membrane, a micro-pore and a micropillar, wherein the capture binder is placed and fixed to the reaction region.

According to an aspect of another exemplary embodiment, there is provided a method for measurement of cholesterol, including: injecting a blood sample into a microfluidic device; transporting a supernatant separated from the blood sample into a reaction chamber that contains a capture binder; combining the non-HDL in the supernatant with the capture binder; transporting HDL not combined with the capture binder into a first detection chamber; transferring an elution buffer from a buffer chamber to the reaction chamber to disassociate the non-HDL from the capture binder; transporting the non-HDL dissociated from the capture binder into a second detection chamber; and determining a concentration of cholesterol in the blood sample through reaction of a cholesterol measurement reagent contained in each of the first and second detection chambers with the HDL and non-HDL in the first and second detection chambers, respectively.

The capture binder may include at least one substance selected from a group consisting of antibodies, antigens, receptors, ligands, oligonucleotides, haptens and aptamers.

The capture binder may be specifically combined with an Apo-B protein of a lipoprotein in the blood sample to capture the non-HDL and separate the non-HDL from the HDL.

The capture binder may be bonded to a solid phase including agarose gel or polymer beads; however, the capture binder is not particularly limited to such forms.

The reaction chamber may include a reaction region in which the capture binder is placed and fixed thereto.

The reaction region may be formed of at least one material selected from a group consisting of a porous membrane, a micro-pore and a micro-pillar.

BRIEF DESCRIPTION OF THE DRAWINGS

The above and/or other aspects will become apparent and more readily appreciated from the following description of exemplary embodiments, taken in conjunction with the accompanying drawings, of which.

DETAILED DESCRIPTION OF THE PREFERRED EMBODIMENTS

Hereinafter, exemplary embodiments will be described with reference to the accompanying drawings. However, at least one exemplary embodiment may be embodied in various other forms, which are not particularly restricted to those described herein.

According to an exemplary embodiment, a device for measurement of cholesterol is a microfluidic device having at least one microfluidic structure that includes multiple chambers. At least one channel interconnects the chambers, and at least one valve opens and closes the at least one channel. The microfluidic device further includes: a reaction chamber containing a capture binder specifically combined with apolipoprotein in order to allow the capture binder to be combined with lipoprotein in blood; a buffer chamber connected with the reaction chamber and containing an elution buffer; and multiple detection chambers connected with the reaction chamber and containing a cholesterol measurement reagent, wherein fluid transfer between the reaction chamber, buffer chamber and detection chambers is controlled using the at least one valve.

Figure 1:
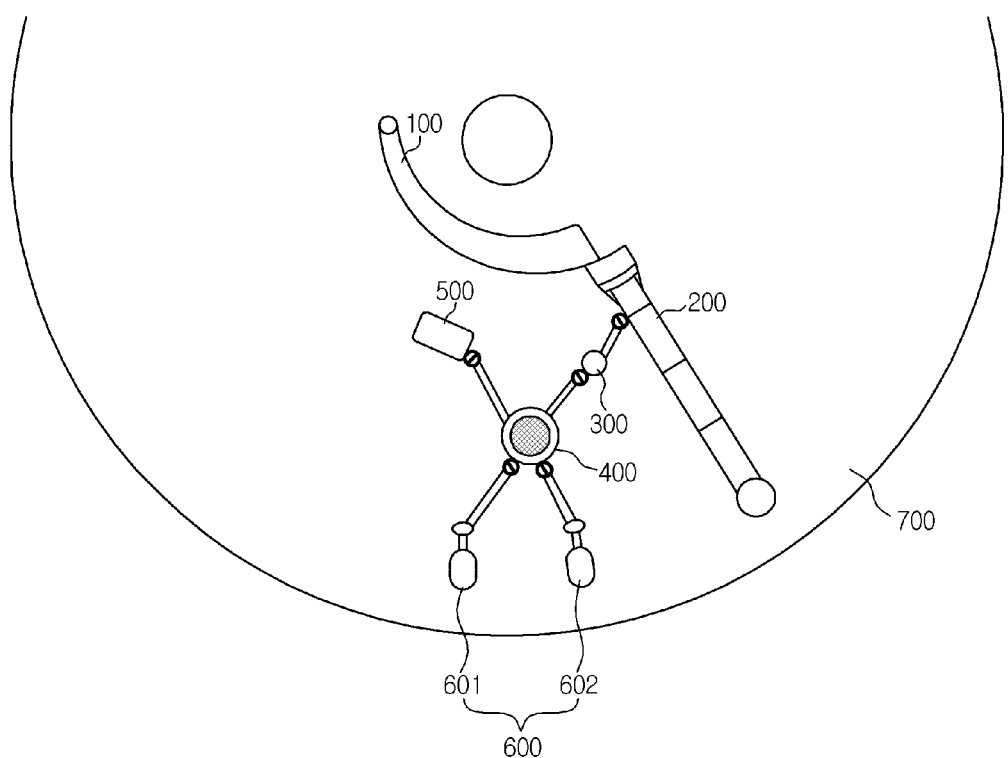
FIG. 1 is a schematic view illustrating the construction of a cholesterol measurement apparatus, according to an exemplary embodiment.

FIG. 1 is a schematic view illustrating the configuration of a cholesterol measurement apparatus, according to an exemplary embodiment.

The same numerical symbols in the drawings refer to substantially the same constitutional elements. Separate structures such as a chamber, a channel, and the like are simply illustrated, and dimensional ratios of the same may be different from real scales thereof, instead being enlarged or reduced. In phrases such as 'microfluidic device,' 'microparticle,' etc., 'micro' is not limitedly construed as a size unit, but used in contrast with 'macro.'

The cholesterol measurement apparatus according to the exemplary embodiment may be a microfluidic device having a microfluidic structure that includes a platform, multiple chambers configured on the platform, at least one channel through which the chambers are interconnected, at least one valve for opening and closing the channels, as well as a detection unit (not shown).

The platform used in the exemplary embodiment may include a circular disc-type platform. However, the shape of the platform is not particularly limited to a circular disc shape. The platform may be formed using acryl or other plastic materials, each of which is easily formable and has a biologically inactive surface. However, a raw material for fabrication of the platform is not particularly limited and may include any materials with chemical or biological stability, optical transparency and/or mechanical workability. That is, the platform may be fabricated using at least one material selected from a variety of materials such as plastic, polymethylmethacrylate (PMMA), glass, mica, silica, or a silica wafer material. The plastic material is used in view of economical merits or simple workability. Commonly available plastic materials include polypropylene, polyacrylate, polyvinylalcohol, polyethylene, PMMA, polycarbonate, etc.

Also, the platform may include multiple layers of plates. If a relief structure corresponding to a chamber or a channel is formed on a side at which two plates face each other, and two or more relief structures are combined, an empty space and/or channel may be provided inside the platform. Such combination of plates may be achieved using an adhesive, a two-sided adhesive tape, ultrasonic welding, etc.

One or more microfluidic structures may be provided on the platform. For instance, after partitioning the platform into several sections, individual microfluidic structures may be provided independently of one another on the respective sections.

The term 'microfluidic structure' as used herein refers to a general structure which includes of a plurality of chambers, channels and valves, that induces a fluid flow, as opposed to a particular structural substance. Therefore, the 'microfluidic structure' may form a specific unit with different functions or performances according to the alignment of chambers, channels and/or valves, and/or kinds of materials received in the structure.

If centrifugal force is applied as a driving pressure to transport a fluid, a rotational disc-type platform may be used. However, a shape of the platform is not particularly limited to the disc-type. That is, it is not required to be a complete circular disc capable of rotating by itself, as a rotatable disc formed into separate sectors and placed on a rotational frame may be adopted as the rotational body. A driving unit (not shown) may also be used to facilitate high velocity rotation of the platform.

Referring to FIG. 1, the cholesterol measuring apparatus may include a sample chamber 100, a sample separation unit 200 and a supernatant metering chamber 300.

The sample chamber 100 may provide an empty space in which a fluid-type sample (or a liquid specimen) such as blood is contained.

The sample chamber 100 may include a sample introduction inlet (not shown) through which the sample is introduced, and a sample receiving unit (not shown). The sample receiving unit also has an outlet (not shown) connected to the separation chamber 200, and the outlet may have a valve (not shown) mounted thereon in order to control flow of the fluid sample from the sample chamber 100 to the sample separation unit 200. The valve may control the fluid as it passes through a channel. In one exemplary embodiment, such a valve may be selected from different types of microfluidic valves. For example, the valve may include a so-called 'normally-closed valve' wherein a channel of the valve is normally closed to prevent a fluid from flowing there through, and is only opened by external power. In particular, the valve may be formed of a mixture including a phase transition material and a heating fluid. Such a phase transition material may include wax, gel or thermoplastic resin. An example of the wax is paraffin wax, and the gel may include, for example, polyacrylamide, polyacrylate, polymethacrylate, polyvinylamide, etc. Also, the thermoplastic resin may include, for example, cyclic olefin copolymer (COC), polymethylmethacrylate (PMMA), polycarbonate (PC), polystyrene (PS), polyoxymethylene (POM), perfluoroalkoxy (PFA), polyvinylchloride (PVC), polypropylene (PP), polyethylene terephthalate (PET), polyetheretherketone (PEEK), polyamide (PA), polysulfone (PSU), polyvinylidene fluoride (PVDF), and so forth. The heating fluid may include a hydrophobic carrier oil and micro-heating particles dispersed in the carrier oil. Each of the micro-heating particles may have a diameter ranging from several tens to several hundreds of nanometers. When the micro-heating particles receive energy through, for example, laser beam irradiation, a temperature of the micro-heating particles is rapidly raised, in turn generating heat. The micro-heating particles may be ferromagnetic metal oxide microparticles. As an external energy source to supply energy to the valve, a laser source having a laser diode to emit a laser beam to a solidified valve may be used. When the solidified valve is irradiated with the laser beam, the valve is fused and fluidized by the external energy applied through the laser beam, thus rapidly expanding to control opening and closing of the channel. Between the sample introduction inlet and the sample receiving unit, there may be provided an alternative structure capable of generating capillary pressure that allows a fluid sample to flow into the sample receiving unit by injection pressure of the sample through the sample introduction inlet. The alternative structure may also block reverse flow of the sample from the sample receiving unit toward the sample introduction inlet. In other words, the alternative structure serves as a capillary valve to pass the sample through the valve only when a desired pressure level is applied.

The sample separation unit 200 is positioned downstream of the sample chamber 100 and is connected to the same through a channel. The sample separation unit 200 receives a fluid sample such as blood transported from the sample chamber 100 and separates the same into a supernatant (i.e., serum, plasma, etc.) and a precipitate (i.e., blood cells) by centrifugation. The sample separation unit 200 may be configured in different forms. The sample separation unit 200 may include a supernatant collector (not shown) and a precipitate collector (not shown) in a space being formed at an end of the supernatant collector to collect a precipitate with relatively high specific gravity. The supernatant collector may have a channel (not shown) for dispensing the centrifuged supernatant into a reaction chamber 400. A valve (not shown) may control the fluid flow through this channel as well. The valve may be any one of a variety of types of microfluidic valves, as discussed above. For example, the valve may include a so-called 'normally-closed valve' wherein a channel of the valve is normally closed to prevent a fluid from flowing unless the valve is opened by external power.

A supernatant metering chamber 300 may be placed between the sample separation unit 200 and the reaction chamber 400 to measure an amount of the supernatant. A volume of the supernatant metering chamber 300 may be sufficient to contain a certain amount of the supernatant required for testing. At an exit point of the supernatant metering chamber 300, a control valve for controlling the flow of fluid out of the chamber may be provided. As described above, the valve may be a normally-closed valve. The supernatant metering chamber 300 may be connected with the reaction chamber 400 through a channel. Although not shown in the drawings, an additional chamber and a corresponding fluid path connected with the additional chamber may be provided between the sample separation unit 200 and the supernatant metering chamber 300 to receive an excess amount of fluid remaining after metering the supernatant.

Referring to FIG. 1, the cholesterol measurement apparatus may further include a reaction chamber 400, a buffer chamber 500 and a detection chamber 600, as well as a detection unit (not shown).

The reaction chamber 400 is placed downstream of the sample separation unit 200 and connected to the same through a channel, and may contain a capture binder 401 (see FIG. 2) to be specifically combined with an apolipoprotein component of lipoprotein in a fluid sample such as blood.

The reaction chamber 400 may be a structure for the separation of lipoprotein contained in the supernatant by using the capture binder 401 to create an antigen-antibody response, ligand-receptor bonding, etc to the lipoprotein.

The capture binder 401 may act as a capture probe for analysis of analytes, and the capture binder 401 may include various materials such as antibodies, antigens, receptors, ligands, oligonucleotides, haptens and aptamers, etc., dependent on different analytes. For instance, if the analyte is a carbamate insecticide, the capture binder may be acetylcholine esterase (AChE). For the analyte of a specific antigen, a capture antibody may be used as the capture binder.

The capture binder 401 according to one exemplary embodiment may include any antibody, antigen, receptor, ligand, oligonucleotide, hapten or aptamer, which can be specifically combined with lipoprotein in the supernatant.

Cholesterol-containing lipids in blood are usually combined with plasma protein, or apolipoprotein, and present as lipoprotein in blood. Such lipoprotein is generally classified according to density as Chylomicron, VLDL, LDL and HDL.

The capture binder 401 may include a binder that selectively binds to Apolipoprotein-B (Apo-B) (a protein constituent of LDL) in order to allow the binder to be combined with lipoproteins other than HDL (hereinafter referred to as "non-HDL"). Since HDL does not include Apo-B protein, while non-HDL does contain Apo-B protein, a desired binder specific to Apo-B protein may be used in order to capture the non-HDL and separate it from the HDL.

Figure 2:
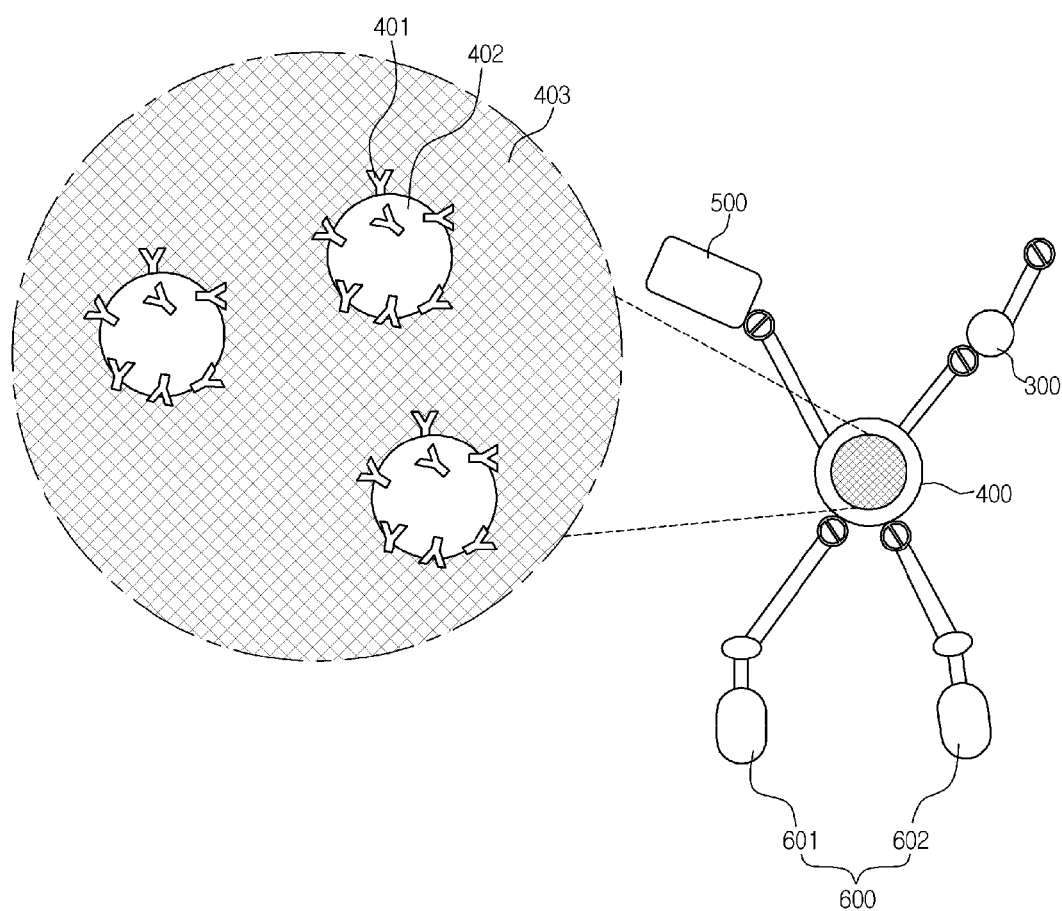
FIG. 2 is a conceptual view illustrating morphology and structure of a reaction chamber, according to an exemplary embodiment.

Referring to FIG. 2, the capture binder 401 may also be bonded to a solid phase 402 including agarose gel or polymer beads; however, the capture binder is not particularly limited to such forms. Furthermore, the capture binder 401 may be placed and fixed to a reaction region 403 of the reaction chamber 400.

The reaction region 403 may be formed of at least one material selected from a group consisting of a porous membrane, a micro-pore and a micro-pillar.

The detection chamber 600 containing a cholesterol measurement reagent is placed downstream of the reaction chamber 400 and connected to the same through a channel. The cholesterol measurement reagent may be present in a dried state or in liquid phase, and may include an enzyme, a substrate, an acidity regulator and an excipient, without particular limitation to such materials.

The buffer chamber 500 containing an elution buffer is placed upstream of the reaction chamber 400 and connected to the same through a channel. Such an elution buffer dissociates antibody-antigen bonds or ligand-receptor bonds between the capture binder 401 and Apo-B protein in the non-HDL, in turn enabling dissociation (or degradation) of the non-HDL from the fixed capture binder 401. Alternatively, the elution buffer may include a selective surfactant in order to remove and discharge cholesterol from the non-HDL that was combined with the fixed capture binder 401.

The detection unit (not shown) may be placed outside the microfluidic structure and may be fabricated in plural in order to measure absorbance of light through the detection chamber 600. The detection unit may have at least one light source, at least one light receiving unit corresponding to the light source to receive light passing through the detection chamber 600, and an analysis unit to analyze optical features of the light received by the light receiving unit and to calculate a concentration of an analyte based on the analyzed optical features.

The light source may be a light source flashing at a specific frequency including, for example, a semiconductor light emitting device such as a light emitting diode (LED) or a laser diode, a gas discharge lamp such as a halogen lamp or a xenon lamp, etc. The light receiving unit generates electrical signals according to an intensity of incident light and may include, for example, a depletion layer photodiode, avalanche photodiode (APD), photomultiplier tube (PMT), etc.

In one exemplary embodiment, the light source unit and the light receiving unit may be positioned to face each other in upward-facing and downward-facing positions, respectively, with the microfluidic structure positioned between the two. A light path may be adjusted through a reflecting mirror or light guide member. The analysis unit may calculate a concentration of an analyte contained in the detection chamber 600 on the basis of a pre-determined standard curve plotting expected concentrations for various measured light absorbances, as well as light absorbance received by the light receiving unit.

A fluid is fed into the cholesterol measurement apparatus using a driving pressure such as centrifugal force generated by rotation of a platform, capillary pressure, a pressure generated by an alternative pump, gravity, etc.

Figure 3:
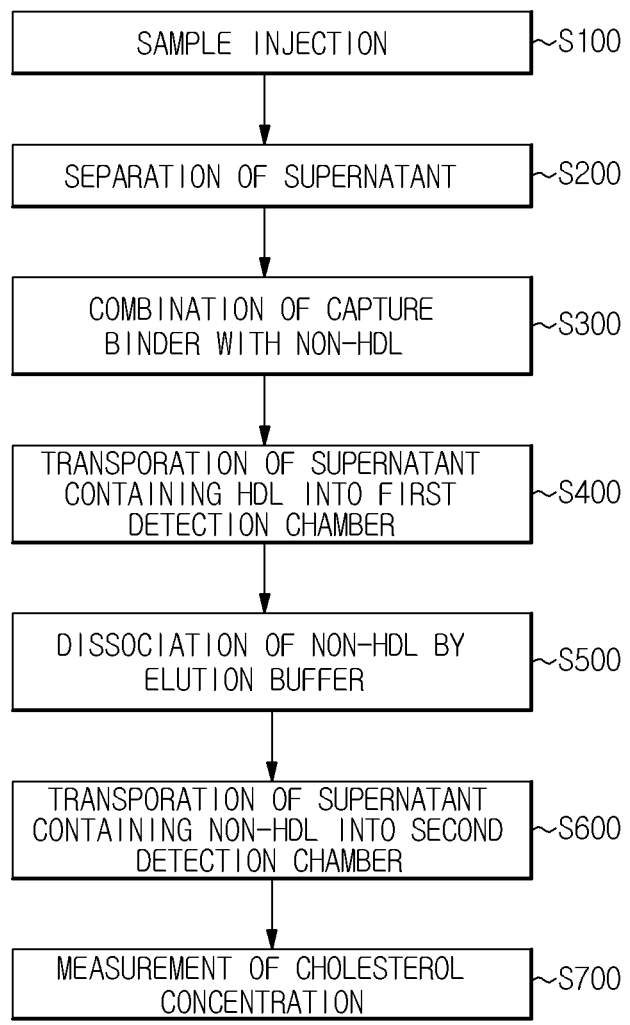
FIG. 3 is a flowchart illustrating a method for measurement of cholesterol, according to an exemplary embodiment.

FIG. 3 is a flowchart illustrating a method for measurement of cholesterol according to an exemplary embodiment.

For example, whole blood extracted from a test subject is injected into a sample chamber 100 (S100), and delivered to a sample separation unit 200 using a driving pressure by opening a closed valve of a channel that connects the sample chamber 100 and the sample separation unit 200.

The whole blood fed into the separation unit 200 is centrifuged by high speed rotation to obtain a supernatant containing a serum or plasma and a precipitate containing blood cells (S200).

During centrifugation, blood cells thicker (or heavier) than the serum or plasma settle downward and move to a precipitate collector (not shown), while the supernatant lighter than the blood cells remains in a supernatant collector (not shown). After centrifugation, the supernatant is transported into a reaction chamber 400 by opening the closed valve of the channel that connects the sample separation unit 200 and the reaction chamber 400.

When the supernatant is delivered from the sample separation unit 200 to the reaction chamber 400, a capture binder 401, which may be placed and fixed with a reaction region 403 of the reaction chamber 400 and bonded to a solid phase 402, is specifically combined with Apo-B protein in non-HDL contained in the supernatant.

In this regard, in order to facilitate combination of the capture binder 401 and the non-HDL, the platform may be shaken several times to the right and left. As a result, HDL continuously remains in the supernatant within the reaction chamber 400 while the non-HDL is combined with the capture binder 401 and fixed to the reaction region 403.

After a desired reaction time for combination of the capture binder 401 and the non-HDL, the supernatant containing the HDL is delivered to a first detection chamber 601 by opening a closed valve of a channel that connects the reaction chamber 400 and the first detection chamber 601 (S400). Transfer of the supernatant containing the HDL into the first detection chamber 601 may separate the HDL from the non-HDL.

After transporting the HDL into the first detection chamber 601, the channel for connecting the first detection chamber 601 and the reaction chamber 400 is closed while another channel for connecting the reaction chamber 400 and a buffer chamber 500 is opened, thereby delivering an elution buffer contained in the buffer chamber 500 to the reaction chamber 400. The elution buffer dissociates antigen-antibody bonds or ligand-receptor bonds between the capture binder 401 and the non-HDL (S500).

After dissociation of the non-HDL from the capture binder 401 using the elution buffer, the non-HDL is delivered to a second detection chamber 602 by opening a closed valve of a channel that connects the reaction chamber 400 to the second detection chamber 602 (S600). Accordingly, the first detection chamber 601 receives the HDL and the second detection chamber 602 receives the non-HDL, thereby physically separating the HDL from the non-HDL.

A cholesterol measurement reagent contained in each of the detection chambers 600 reacts with the HDL and the non-HDL transported into the detection chambers 600, respectively. In addition, a detection unit placed outside a microfluidic structure optically or electrically measures cholesterol reacted with the measurement reagent and calculates a concentration of the cholesterol from the measured results, on the basis of a standard curve for HDL cholesterol (S700).

The foregoing apparatus and method for measurement of cholesterol according to the exemplary embodiments may improve accuracy in measurement of HDL cholesterol and may simultaneously determine a concentration of non-HDL cholesterol and the entire cholesterol concentration, thereby considerably reducing time and procedures required to determine a concentration of cholesterol in blood.

Although a few exemplary embodiments have been shown and described, it would be appreciated by those skilled in the art that changes may be made in these embodiments without departing from the principles and spirit of the inventive concept, the scope of which is defined in the claims and their equivalents.

What is claimed is:

1. A cholesterol measurement apparatus comprising:
a microfluidic device comprising a plurality of chambers and at least one channel through which the plurality of chambers are interconnected,
wherein the plurality of chambers comprise:
a sample chamber;
a separation chamber connected to sample chamber;
a reaction chamber which contains a capture binder;
a metering chamber interconnecting the separation chamber and the reaction chamber;
a buffer chamber which contains an elution buffer and is connected to the reaction chamber; and
at least one detection chamber which contains a cholesterol measurement reagent and is connected to the reaction chamber.

2. The cholesterol measurement apparatus according to claim 1, wherein the microfluidic device further comprises at least one valve which controls transfer of a fluid between the plurality of chambers.

3. The cholesterol measurement apparatus according to claim 2, wherein the at least one valve comprises a mixture of a phase transition material and a fluid.

4. The cholesterol measurement apparatus according to claim 3, wherein the phase transition material comprises at least one material selected from a group consisting of wax, gel and thermoplastic resin.

5. The cholesterol measurement apparatus according to claim 3, wherein the fluid comprises carrier oil and micro-heating particles dispersed in the carrier oil, and the micro-heating particles are metal oxide microparticles.

6. The cholesterol measurement apparatus according to claim 3, further comprising an external energy source which supplies energy to operate the valve.

7. The cholesterol measurement apparatus according to claim 6, wherein the external energy source is a laser source.

8. The cholesterol measurement apparatus according to claim 1, wherein the capture binder comprises at least one substance selected from a group consisting of antibodies, antigens, receptors, ligands, oligonucleotides, haptens and aptamers.

9. The cholesterol measurement apparatus according to claim 1, wherein the capture binder is combined with an Apo-B protein of a lipoprotein in a fluid sample to capture non-high density lipoprotein (HDL) and separate the non-HDL from HDL.

10. The cholesterol measurement apparatus according to claim 1, wherein the capture binder is bonded to a solid phase comprising agarose gel or polymer beads.

11. The cholesterol measurement apparatus according to claim 1, wherein the reaction chamber comprises a reaction region in which the capture binder is placed and fixed thereto.

12. The cholesterol measurement apparatus according to claim 11, wherein the reaction region is formed of at least one material selected from a group consisting of a porous membrane, a micro-pore and a micro-pillar.

13. A centrifugal cholesterol measurement apparatus comprising:
a microfluidic device comprising a rotational body including a plurality of chambers and at least one channel through which the plurality of chambers are interconnected,
wherein the plurality of chambers comprise:
a sample chamber;
a separation chamber connected to the sample chamber;
a reaction chamber which contains a capture binder;
a metering chamber interconnecting the separation chamber and the reaction chamber;
a buffer chamber which contains an elution buffer and is connected to the reaction chamber; and
at least one detection chamber which contains a cholesterol measurement reagent and is connected to the reaction chamber.

14. The centrifugal cholesterol measurement apparatus according to claim 13, wherein the microfluidic device further comprises at least one valve which controls transfer of a fluid between the plurality of chambers.

15. The centrifugal cholesterol measurement apparatus according to claim 14, wherein the valve comprises a mixture of a phase transition material and a heating fluid.

16. The centrifugal cholesterol measurement apparatus according to claim 15, wherein the phase transition material comprises at least one material selected from a group consisting of wax, gel and thermoplastic resin.

17. The centrifugal cholesterol measurement apparatus according to claim 15, wherein the heating fluid comprises carrier oil and micro-heating particles dispersed in the carrier oil, and the micro-heating particles are metal oxide microparticles.

18. The centrifugal cholesterol measurement apparatus according to claim 15, further comprising an external energy source which supplies energy to operate the valve.

19. The centrifugal cholesterol measurement apparatus according to claim 18, wherein the external energy source is a laser source.

20. The centrifugal cholesterol measurement apparatus according to claim 13, wherein the capture binder includes at least one substance selected from a group consisting of antibodies, antigens, receptors, ligands, oligonucleotides, haptens and aptamers.

21. The centrifugal cholesterol measurement apparatus according to claim 13, wherein the capture binder is bonded to a solid phase comprising agarose gel or polymer beads.

22. The centrifugal cholesterol measurement apparatus according to claim 13, wherein the reaction chamber comprises a reaction region in which the capture binder is placed and fixed thereto, and
wherein the reaction region is formed of at least one material selected from a group consisting of a porous membrane, a micro-pore and a micro-pillar.

23. A method for measurement of cholesterol, the method comprising:
injecting a blood sample into a microfluidic device;
transporting a supernatant separated from the blood sample into a reaction chamber of the microfluidic device that contains a capture binder;
combining non-high density lipoprotein (HDL) in the supernatant with the capture binder;
transporting HDL not combined with the capture binder into a first detection chamber of the microfluidic device;
transferring an elution buffer from a buffer chamber of the microfluidic device to the reaction chamber to disassociate the non-HDL from the capture binder;
transporting the non-HDL dissociated from the capture binder into a second detection chamber of the microfluidic device; and
determining a concentration of cholesterol in the blood sample through reaction of a cholesterol measurement reagent contained in each of the first and second detection chambers with the HDL and non-HDL in the first and second detection chambers, respectively.

24. The method according to claim 23, wherein the capture binder comprises at least one substance selected from a group consisting of antibodies, antigens, receptors, ligands, oligonucleotides, haptens and aptamers.

25. The method according to claim 23, wherein the capture binder is combined with an Apo-B protein of a lipoprotein in the blood sample to capture non-HDL and separate the non-HDL from the HDL.

26. The method according to claim 23, wherein the capture binder is bonded to a solid phase comprising agarose gel or polymer beads.

27. The method according to claim 23, wherein the reaction chamber comprises a reaction region in which the capture binder is placed and fixed thereto.

28. The method according to claim 27, wherein the reaction region is formed of at least one material selected from a group consisting of a porous membrane, a micro-pore and a micro-pillar.

\* \* \* \* \*